US00PP28895P3

(12) United States Plant Patent
Danziger

(10) Patent No.: US PP28,895 P3
(45) Date of Patent: Jan. 23, 2018

(54) ***PERICALLIS* PLANT NAMED 'DPRIMBLUBR'**

(50) Latin Name: *Pericallis hybrida*
Varietal Denomination: DPRIMBLUBR

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 56 days.

(21) Appl. No.: 14/999,429

(22) Filed: May 3, 2016

(65) Prior Publication Data

US 2017/0325374 P1 Nov. 9, 2017

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

(56) References Cited

PUBLICATIONS

Tropicos.org. Missouri Botanical Garden. Aug. 17, 2017 <http://www.tropicos.org>. Citation for *Senecio cruentus*.*

* cited by examiner

*Primary Examiner* — Susan McCormick Ewoldt
*Assistant Examiner* — Karen Redden
(74) *Attorney, Agent, or Firm* — Cassandra Bright

(57) ABSTRACT

A new and distinct *Pericallis* cultivar named 'DPRIMBLUBR' is disclosed, characterized by a very compact and mounded habit with dense branching, early flowering and tolerance for powdery mildew. Additionally all flowers are at the same height. The new variety is a *Pericallis*, normally produced as an outdoor garden or container plant.

2 Drawing Sheets

Figure 1:
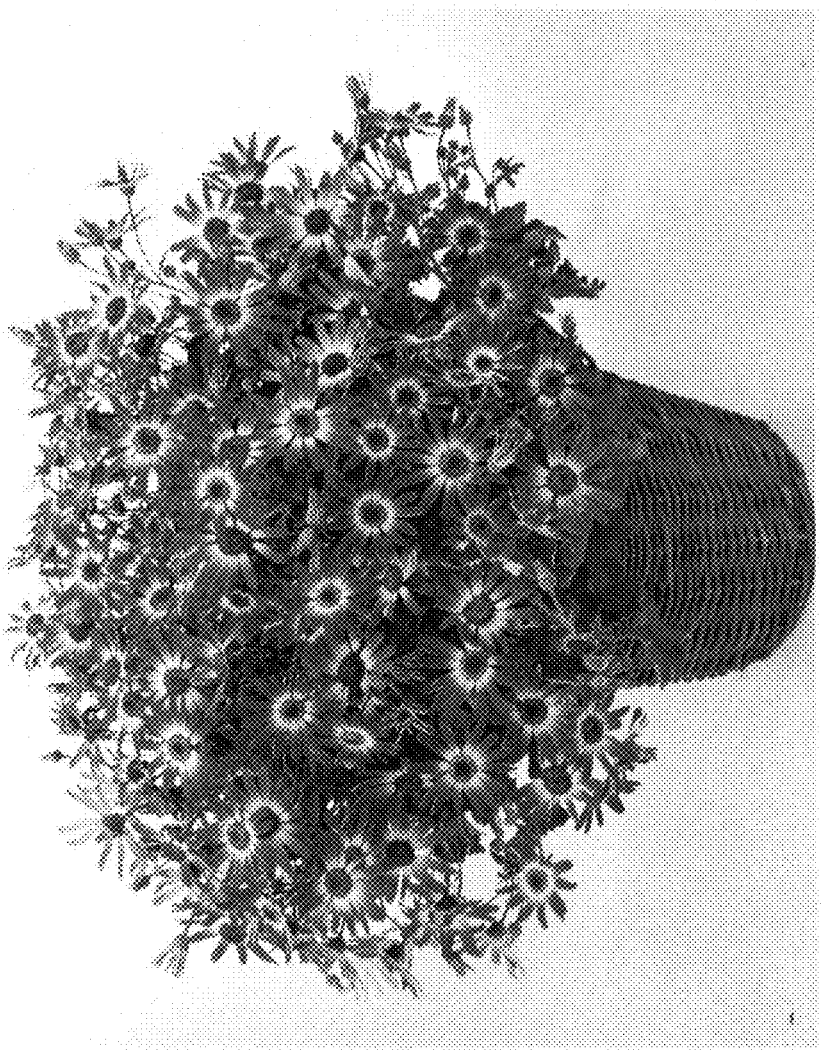

Latin name of the genus and species: *Pericallis hybrida*. Variety denomination: 'DPRIMBLUBR'.

BACKGROUND OF THE INVENTION

The new *Pericallis* cultivar is a product of a planned breeding program conducted by the inventor, Gavriel Danziger in Moshav Mishmar Hashiva, Israel. The objective of the breeding program was to produce new *Pericallis* varieties. The open pollination resulting in this new variety was made during May of 2012.

The seed parent is the unpatented, propriety variety referred to as *Pericallis* 'CN-12-251'. The pollen parent is unknown as it was an open pollination breeding program. The new variety was discovered in December of 2013 by the inventor in a group of seedlings resulting from the 2012 crossing, in a greenhouse in Moshav Mishmar Hashiva, Israel.

Asexual reproduction of the new cultivar 'DPRIMBLUBR' was first performed by terminal vegetative cuttings during January of 2014 at a greenhouse in Moshav Mishmar Hashiva, Israel. Subsequent propagation by vegetative cuttings has shown that the unique features of this cultivar are stable and reproduced true to type in multiple generations.

SUMMARY OF THE INVENTION

The cultivar 'DPRIMBLUBR' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DPRIMBLUBR' These characteristics in combination distinguish 'DPRIMBLUBR' as a new and distinct *Pericallis* cultivar:

1. Very compact and mounded habit.
2. Early flowering.
3. All the flowers occurring evenly at the same height.
4. Tolerance to powdery mildew.

PARENT COMPARISON

Plants of the new cultivar 'DPRIMBLUBR' are similar to plants of the seed parent, most horticultural characteristics, however, plants of the new cultivar 'DPRIMBLUBR' differ in the following;

1. More compact habit than the seed parent.
2. Blooms earlier than the seed parent.
3. More floriferous than the seed parent.

COMMERCIAL COMPARISON

Plants of the new cultivar 'DPRIMBLUBR' can be compared to the patented commercial variety *Pericallis* 'SUSENERABU', U.S. Plant Pat. No. 16,357. These varieties are similar in most horticultural characteristics; however, 'DPRIMBLUBR' differs in the following:

1. Plants of 'DPRIMBLUBR' have smaller flowers than plants of 'SUSENERABU'.
2. Plants of 'DPRIMBLUBR' have a violet blue with white center flower color compared to the light blue flower color of 'SUSENERABU'.
3. Plants of 'DPRIMBLUBR' have smaller ray florets than 'SUSENERABU'.

Plants of the new cultivar 'DPRIMBLUBR' can also be compared to the unpatented commercial variety *Pericallis* 'Spring Touch Grape'. These varieties are similar in most horticultural characteristics; however, 'DPRIMBLUBR' differs in the following:

1. Plants of 'DPRIMBLUBR' have smaller flowers than plants of 'Spring Touch Grape'.
2. Plants of 'DPRIMBLUBR' are more compact than plants of 'Spring Touch Grape'.
3. Plants of 'DPRIMBLUBR' bloom earlier than plants of 'Spring Touch Grape'.
4. Plants of 'DPRIMBLUBR' have a violet blue with white centered flower compared to the dark purple flower color of 'Spring Touch Grape'.

BRIEF DESCRIPTION OF THE PHOTOGRAPHS

The accompanying photograph in FIG. 1 illustrates in full color a typical plant of 'DPRIMBLUBR' grown in 13 cm pots outdoors in Moshav Mishmar Hashiva, Israel.

Figure 2:
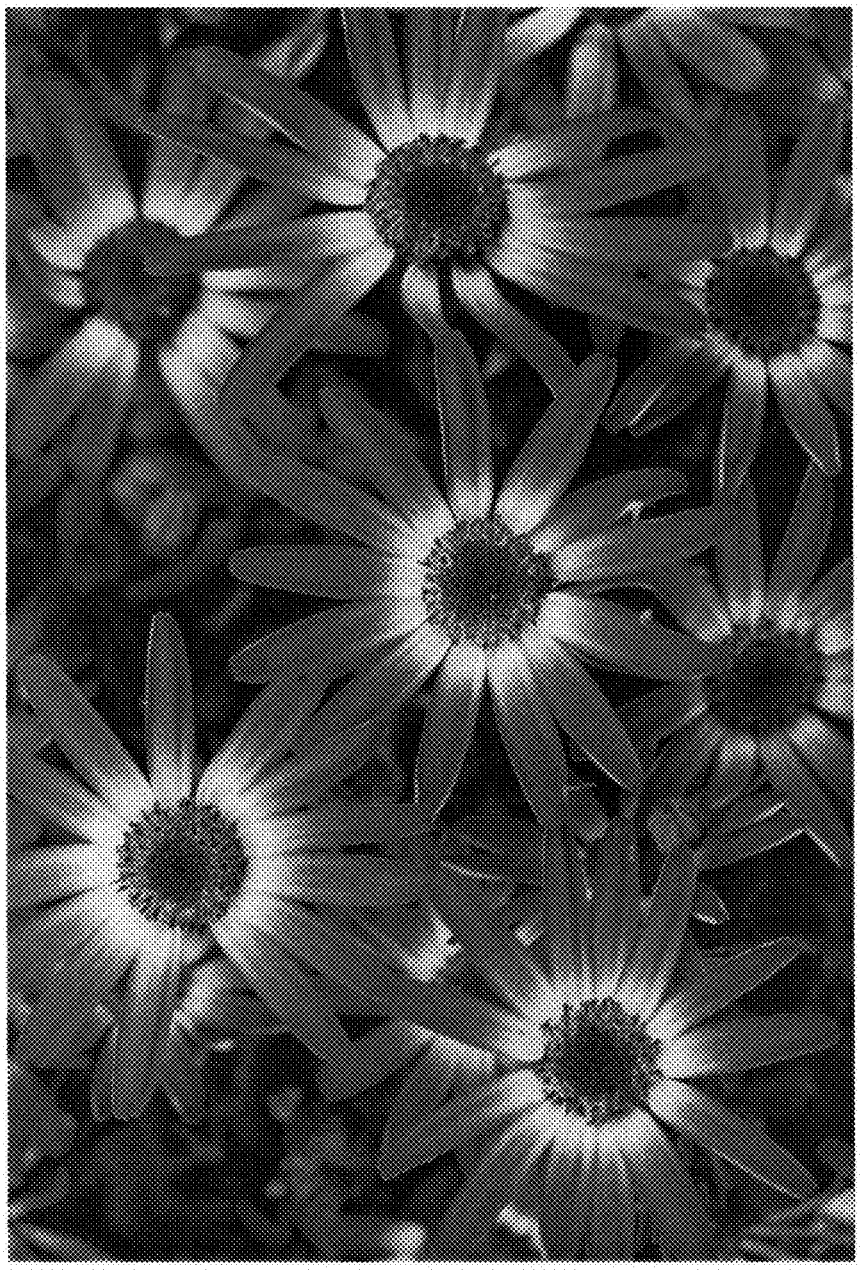

FIG. 2 illustrates in full color multiple typical inflorescence of 'DPRIMBLUBR'. Age of the plant photographed is approximately 11 weeks from a rooted cutting in a 13 cm pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DPRIMBLUBR' plants grown in a greenhouse in Moshav Mishmar Hashiva, Israel, under natural lighting. Measurements were taken during Spring of 2016. The plants were approximately 11 weeks old from a rooted cutting in a 13 cm pot. The growing temperature ranged from approximately 15° C. to 20° C. during the days, 7° C. to 12° C. during the nights. Measurements and numerical values represent averages of typical plant types.

Botanical classification: *Pericallis hybrida* 'DPRIMBLUBR'.

PROPAGATION

Time to rooting: 14 days at approximately 18° C.

Root description: Fine, fibrous and white, color not accurately measured with R.H.S. chart.

PLANT

Growth habit: Upright.
Height: Approximately 24 cm.
Plant spread: Approximately 33 cm.
Growth rate: Moderate growth.
Branching characteristics: Freely branching.
Length of lateral branches: Approximately 19 cm.
Diameter of lateral branches: Approximately 0.3 cm.
Texture of lateral branches: Slightly pubescent.
Internode length: Approximately 2.5 cm.
Strength of stem: Flexible.
Color of lateral branches: Near Yellow-Green 146C.
Aspect/angle of branches: 30.
Number of leaves per lateral branch: Approximately 6.

FOLIAGE

Leaf:
- *Arrangement*.—Alternate, simple.
- *Average length*.—Approximately 6 cm.
- *Average width*.—Approximately 6.5 cm.
- *Shape of blade*.—Sinuate.
- *Description of lobes*.—Shallowly lobed.
- *Apex*.—Acute.
- *Base*.—Sagittate.
- *Attachment*.—Petiolate.
- *Margin*.—Entire.
- *Texture of top surface*.—Glabrous, coarse.
- *Texture of bottom surface*.—Smooth, wooly, obvious venation pattern.
- *Appearance top surface*.—Matte.
- *Appearance bottom surface*.—Matte, noticeable veins, wool-like coating.
- *Leaf internode length*.—Approximately 4.2 cm.
- *Color*.—Young foliage upper side: Near Yellow-Green 146B. Young foliage under side: Near Yellow-Green 147C. Mature foliage upper side: Near Yellow-Green 146A. Mature foliage under side: Near Yellow-Green 147C.
- *Venation*.—Type: Palmate. Venation color upper side: Near Yellow-Green 147B. Venation color under side: Near Yellow-green 147C.

Petiole:
- *Petiole*.—Fleshy, shiny slightly ribbed longwise, flex.
- *Length*.—1.8 cm.
- *Diameter*.—0.2 cm.
- *Pubescence*.—No.
- *Color*.—Near Yellow-Green 147C.

FLOWER

Bloom period: Late Winter to early Summer in Moshav, Mishmar Hashiva, Israel.

Bud:
- *Bud shape*.—Globular.
- *Bud length*.—Approximately 0.5 cm.
- *Bud diameter*.—Approximately 0.3 cm.
- *Bud color*.—Near Green 138B.

Inflorescence:
- *Form*.—Composite inflorescences positioned above the foliar plane.

Flower:
- *Diameter of entire flower*.—Approximately 3.7 cm.
- *Depth of flower*.—Approximately 0.4 cm.
- *Width of disc*.—Approximately 1 cm.
- *Depth of disc*.—Approximately 0.5 cm.

Ray florets:
- *Number of ray florets*.—Average 13.
- *Length*.—Approximately 2 cm.
- *Width*.—Approximately 0.7 cm.
- *Apex shape*.—Rounded.
- *Base*.—Attenuate.
- *Margin*.—Entire.

Color:
- *Ray florets*.—Upper surface at first opening: Near Violet N88A RHS and from White 155B at base. Upper surface at maturity: Near Violet N88A RHS and from White 155C at base. Upper surface at fading: Near Violet N88B RHS and White 155C at base. Under surface at first opening: Near Violet-blue 91B RHS and White 155A at base. Under surface at maturity: Near Violet N88C RHS and White 155C at base. Under surface at fading: Near Violet N88C BRHS and White 155B at base.

*Disc florets*.—Number of Disc Florets: 120. Length: Approximately 0.7 cm. Width: Approximately 0.1 cm. Shape: Tubular. Margin: Entire.

*Color*.—At first opening: Near White 155B and Violet-Blue 96A. At maturity: Near White 155A and Violet-Blue 96A. At fading: Near White 155A and Violet-Blue 96A.

Fragrance: None.

Phyllaries/involucral bracts:

*Number*.—Approximately 14.
*Sepal length*.—Approximately 0.6 cm.
*Sepal width*.—Approximately 0.2 cm.
*Sepal texture*.—Smooth, glabrous.
*Apex shape*.—Acute.
*Margin*.—Entire.
*Color*.—Near Yellow-Green 144A.

Peduncle:

*Peduncle length*.—Approximately 2.5 cm.
*Peduncle diameter*.—Approximately 0.2 cm.
*Angle*.—Approximately 30 degrees from center of whorl.
*Color*.—Near Yellow-Green 148A.
*Peduncle texture*.—Smooth, glabrous.

REPRODUCTIVE ORGANS

Disc florets:

*Androecium*.—Present on disc florets only.
*Stamens*.—*About* 60.
*Anther shape*.—Rounded.
*Anther length*.—Approximately 0.1 cm.
*Anther color*.—Near Purple-Violet 81A.
*Pollen quantity*.—Abundant.

Gynoecium:

*Pistil number*.—13.
*Pistil shape*.—Forked.
*Pistil length*.—Approx. 0.5 cm.
*Style length*.—Approx. 0.3 cm.
*Style color*.—Near Yellow-Green 145D.
*Stigma shape*.—Decurrent.
*Stigma color*.—Near Purple-Violet 80.
*Ovary diameter*.—0.2 cm.
*Ovary color*.—Near Yellow-Green 144A.

Ray florets:

Androecium: Absent.

Gynoecium:

Pistil number.—1.
*Pistil shape*.—Linear.
*Pistil length*.—Approx. 0.15 cm.
*Style length*.—Approx. 0.15 cm.
*Style color*.—Near Yellow-Green 145D.
*Stigma shape*.—Outwardly curved forked.
*Stigma color*.—Near Violet-Blue N92A.
*Ovary diameter*.—0.1 cm.
*Ovary color*.—Near Yellow-Green 146B.

OTHER CHARACTERISTICS

Disease and pest resistance: Better resistance to powdery mildew than typical of known *Pericallis* varieties. Neither resistance nor susceptibility to additional normal diseases and pests of *Pericallis* has been observed.

Drought tolerance and cold tolerance: Low tolerance for cold or drought.

Fruit/seed production: Abundant seed production.

*Shape*.—Oblong.
*Color*.—Near Brown 200B.
*Size*.—Length: 0.2 cm. Width: 0.05 cm.

What is claimed is:

1. A new and distinct cultivar of *Pericallis* plant named 'DPRIMBLUBR' as herein illustrated and described.

* * * * *